United States Patent [19]
Colavecchio

[11] Patent Number: 5,256,142
[45] Date of Patent: Oct. 26, 1993

[54] INJECTOR ADMINISTERING SUBCUTANEOUS INJECTIONS WITHOUT A NEEDLE AND WITH A ONE-SHOT CAP

[75] Inventor: Antonio Colavecchio, Sagrado D'Isonzo, Italy

[73] Assignee: SICIM SpA, Romans D'Isonzo, Italy

[21] Appl. No.: 914,407

[22] Filed: Jul. 17, 1992

[30] Foreign Application Priority Data

Aug. 6, 1991 [IT] Italy .................. UD91A000128

[51] Int. Cl.⁵ .............................. A61M 5/30
[52] U.S. Cl. ........................... 604/68; 604/71; 604/110
[58] Field of Search .................. 604/68–72, 604/110

[56] References Cited

U.S. PATENT DOCUMENTS

| | | | |
|---|---|---|---|
| 2,699,166 | 1/1955 | Dickinson, Jr. et al. | 604/70 |
| 3,320,954 | 5/1967 | Cowley | 604/110 |
| 3,557,784 | 1/1971 | Shields | 604/68 |
| 3,945,383 | 3/1976 | Bennett et al. | 604/72 |
| 4,027,669 | 6/1977 | Johnston et al. | 604/110 |
| 4,874,367 | 10/1989 | Edwards | 604/68 |
| 4,966,581 | 10/1990 | Landau | 604/72 |
| 5,000,738 | 3/1991 | LaVallo et al. | 604/110 |
| 5,026,343 | 6/1991 | Holzer | 604/68 |
| 5,062,830 | 11/1991 | Dunlap | 604/68 |

FOREIGN PATENT DOCUMENTS

| | | | |
|---|---|---|---|
| 1256343 | 6/1989 | Canada | 604/71 |
| 406778 | 7/1990 | European Pat. Off. | |
| 959397 | 6/1964 | United Kingdom | |

Primary Examiner—Ralph Lewis
Attorney, Agent, or Firm—Antonelli, Terry Stout & Kraus

[57] ABSTRACT

Injector administering subcutaneous injections without a needle and with a one-shot cap. The injector (11) includes an injection head (16), a chamber (27) to contain medicament which cooperates with a piston (28), an outlet aperture (15) for the medicament, means (30) to convey the medicament into the containing chamber (27), means to compress means which expel the medicament and a cocking and trigger assembly to actuate the expulsion means. The injector may also include means to measure the quantity of medicament charged and possibly means to limit the charging. In cooperation with the injector (11) is a frontal replaceable one-shot cap (10) with a removable stopper (12) which is broken in a pre-set manner. An axially movable striker (26) is also included and has a first breakage position and a second injection position defined by the replaceable one-shot cap (10). The first breakage position is associated substantially with the position of complete expulsion of the medicament from the containing chamber (27) by the piston (28).

10 Claims, 2 Drawing Sheets

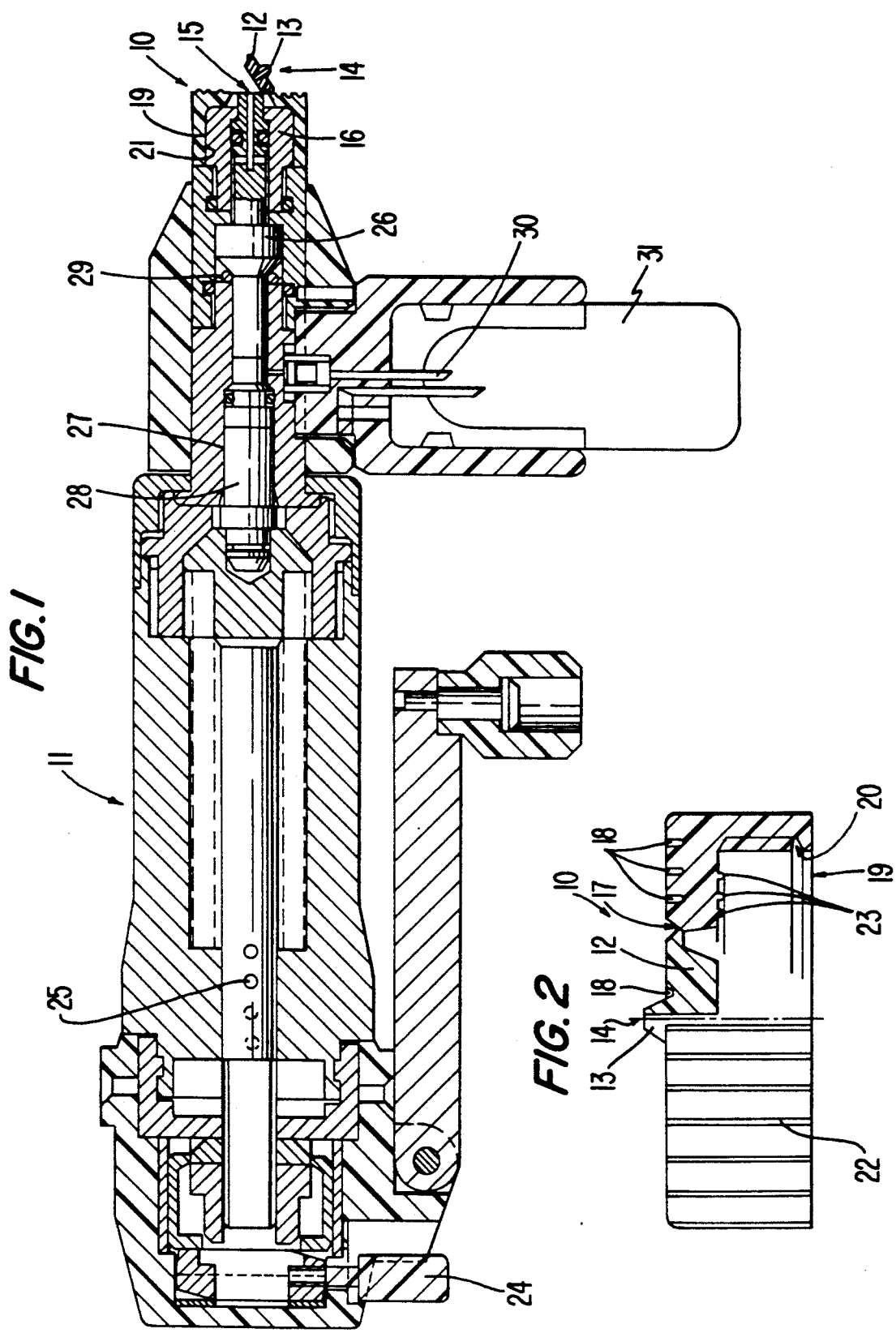

INJECTOR ADMINISTERING SUBCUTANEOUS INJECTIONS WITHOUT A NEEDLE AND WITH A ONE-SHOT CAP

BACKGROUND OF THE INVENTION

1. Field of the Invention

This invention concerns an injector administering subcutaneous injections without a needle and with one-shot cap and concerns also the one-shot caps for subcutaneous injections as set forth in the main claim.

The one-shot cap according to this invention possesses the feature of not being capable of being re-used, while the relative injector cannot be used with an already used one-shot cap or without a one-shot cap, thus preventing any possibility of one patient communicating a disease to another.

The one-shot cap according to this invention can be fitted advantageously to injectors of any known type administering subcutaneous injections without a needle by adapting the head of such injectors suitably.

2. Description of Related Art

The state of the art includes injectors which administer subcutaneous injections and enable the medicament to pass through the skin and to spread in the underlying zone without the part of the body in question being perforated, as happens instead with injections made with traditional syringes.

Injectors administering subcutaneous injections are known to which the one-shot cap according to this invention can be applied advantageously.

With these injectors the medicament is injected without perforating the skin since the medicament itself is expelled at a high pressure from the injector through an aperture of a very small diameter and thus penetrates into the subcutaneous portion in question.

This injector therefore performs the same functions as a normal syringe used for subcutaneous injections but provides the advantage that the injection causes no pain since it is carried out without puncturing the portion of the body in question.

This entails a great advantage, above all for children and for those persons who have of necessity to be often injected for reasons of health.

IT-1.166.326 discloses an injector to administer subcutaneous injections without a needle, whereby the medicament held in an appropriate chamber is expelled through an aperture of a very small diameter.

The medicament is expelled by the action of a piston actuated by previously compressed spring means cooperating with a safety catch system, the whole being adjustable as desired.

The injector disclosed in the above document and administering subcutaneous injections without a needle comprises in reciprocal cooperation and coordination an injection head including a medicament containing chamber in which a small piston able to slide within the chamber cooperates, an aperture for discharge of the medicament, a valve enabling the medicament to pass from phials to the containing chamber with simultaneous selection of the phials themselves and from the containing chamber to the discharge aperture, means to compress spring means which expel the medicament, a cocking and trigger means to actuate the previously compressed spring means, means to measure the quantity of medicament charged, means to limit the charging, safety means, etc.

IT-1.189.884, for which an application for a European patent was published under No.0250022 and a U.S. Pat. No. was granted under No. 4,850,967, discloses other forms of embodiment of an injector to administer subcutaneous injections without a needle, these forms containing further improvements unimportant for the purposes of the present invention and being such that the one-shot cap according to the present invention can be applied advantageously to them.

All the above injectors to administer subcutaneous injections without a needle and other known like or related injectors entail the shortcoming that, when they are used to inject the same medicament, for instance a vaccine, into a plurality of persons, the head of the injector has to be dismantled and replaced on each occasion so that it can be sterilized to prevent any infections.

In fact, even if there is no physical penetration into the skin by any part of these injectors administering subcutaneous injections without a needle, the portion of the injector coming into contact with the skin should be sterilized before each injection for reasons of hygiene too.

The present applicants are not aware of one-shot caps which can be fitted to injectors administering subcutaneous injections without a needle according to this invention, nor are they aware of injectors of the above cited type which cannot perform the injection without having a one-shot cap that is intact.

SUMMARY OF THE INVENTION

The present applicants have designed, tested and embodied this invention so as to obviate the present operations of dismantling, sterilizing and thereafter refitting the head of the injector, these operations taking a long time and being complicated.

The one-shot cap according to this invention can be fitted advantageously, but not only, to all the types of injectors administering subcutaneous injections without a needle which are disclosed in the documents cited above and also to like injectors by means of a prior simple modification of the head of the injector so as to provide for the system of destruction of the one-shot cap after each use of the latter.

As we said above, the one-shot cap according to this invention can also be fitted to all the other known types of injectors administering subcutaneous injections without a needle.

The one-shot cap according to this invention is made advantageously of a plastic material, is fitted to the head of the injector and is the element which contacts the skin of the person being injected.

The fitting of the one-shot cap according to this invention can take place with a bayonet-type attachment, with a screw or catch system, etc.; the fitting system is pertinent only as regards the positioning and retention of the cap on the injector for the necessary time.

The one-shot cap according to the invention contains a hole of a small diameter for the passage of the medicament to be injected and when the one-shot cap has been fitted to the head of the injector, this hole lies in a position coordinated with the aperture in the head of the injector.

The aperture in the head of the injector according to the invention has a diameter such that the injection is not possible unless the one-shot cap is correctly positioned.

The one-shot cap according to the invention contains in the middle of its upper surface a pre-established breakage zone, which defines a removable stopper of a small diameter which is detached at least partly by a striker immediately after injection of the medicament has taken place, thus making impossible the re-use of the one-shot cap.

The one-shot cap according to the invention is packaged advantageously singly by itself alone in a sealed and sterilized container so as to ensure its sterility.

According to a variant the one-shot cap according to the invention contains grooves in its inner surface, which during the fitting of the one-shot cap on the head of the injector cooperate with the terminal portion of the head of the injector and become deformed, thus ensuring the seal engagement of the one-shot cap according to the invention.

According to the invention the head of the injector includes a striker which enables the dose of medicament to be charged and which is located in the injection position by the fitting of the one-shot cap on the injector head. This striker is thrust directly by an injection piston against the removable stopper included in the one-shot cap.

According to a variant the injection piston is equipped in a suitable lower position with a ring abutment, which abuts against one or more small lateral pistons during the forward travel of, and substantially at the end of travel of, the injection piston.

The small lateral pistons are provided at the periphery of the medicament containing chamber in which the injection piston slides and in turn are thrust so as to abut against the striker, thus determining the forward movement of the striker and the resulting breakage of the removable stopper.

BRIEF DESCRIPTION OF THE DRAWINGS

The attached figures which are given as a non-restrictive example, show a preferred embodiment of the invention as follows:

FIG. 1 shows a lengthwise section of an injector equipped with a one-shot cap according to the invention after an injection has been made;

FIG. 2 shows in an enlarged scale a partly cutaway side view of the one-shot cap according to the invention before the cap has been used;

DETAILED DESCRIPTION OF THE PREFERRED EMBODIMENT

Figure 3:
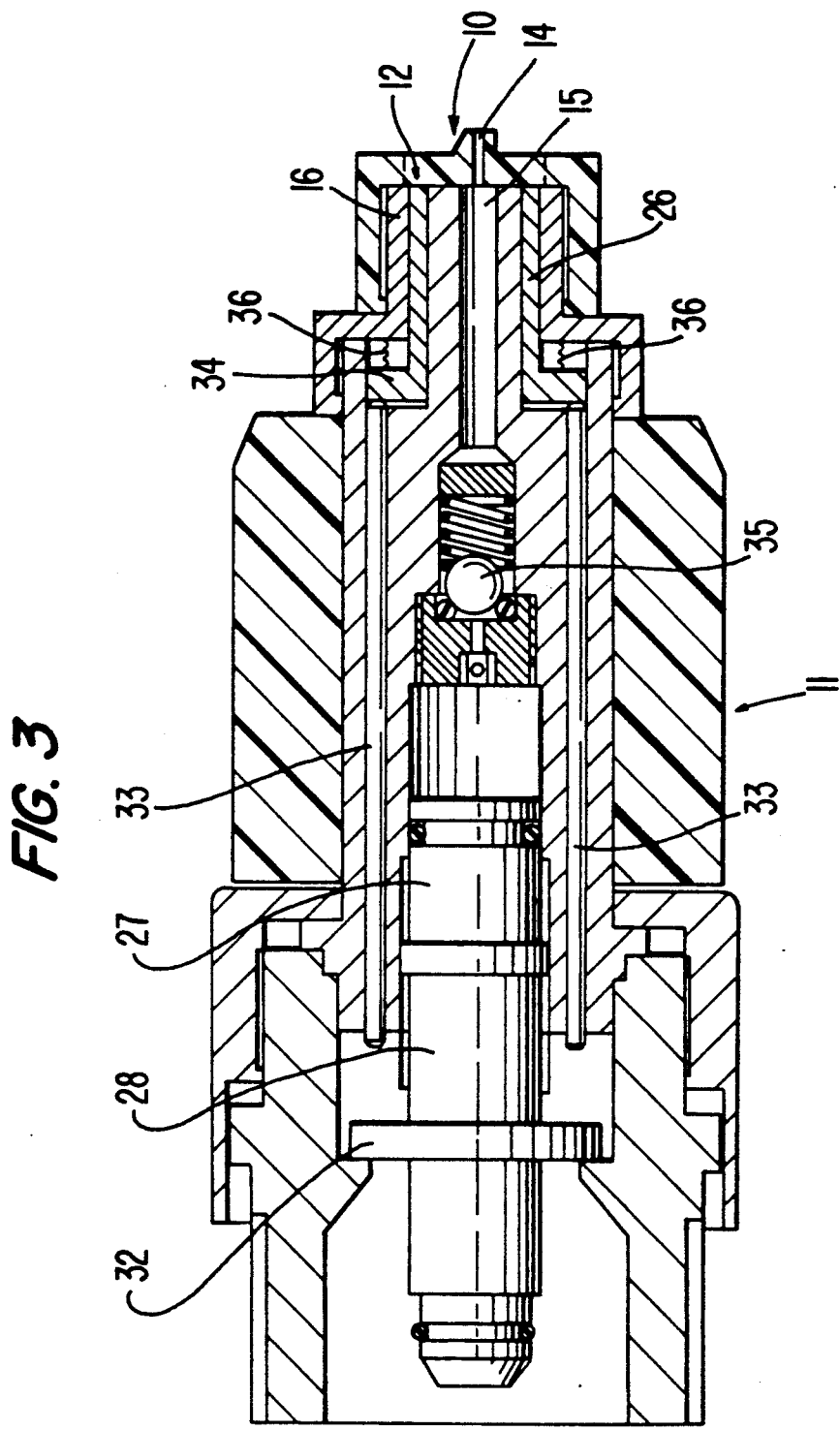
FIG. 3 shows a variant of the injector of FIG. 1 with a detail in an enlarged scale.

In the figures the reference number 10 indicates a one-shot cap according to the invention, which is fitted advantageously to an injector 11 that administers subcutaneous injections without a needle.

In this example the one-shot cap 10 according to the invention is fitted to an injector 11 that administers subcutaneous injections without a needle, the injector 11 being of the type disclosed in EP 0250022, but the cap 10 could be fitted to any other injector which administers subcutaneous injections without a needle.

To be more exact, the one-shot cap 10 according to the invention is fitted to a head 16 of the injector 11 which administers subcutaneous injections without a needle.

In this case, so as to be able to fit the one-shot cap 10 according to the invention to the injector 11 which administers subcutaneous injections without a needle and is of the type disclosed in IT-1166326, the head 16 of the injector 11 has been modified by adding an outer threaded portion 21 which acts as an anchorage means 19, and a striker 26 has been included.

The one-shot cap 10 comprises a removable stopper 12 defined by an attachment lip 17 and also a central, axially perforated protrusion 13 containing a hole 14 of a small diameter, which is positioned in relation to an injection aperture 15 contained in the striker 26.

In this example the one-shot cap 10 shown consists of a plastic material and is produced advantageously by being moulded. In this case the stopper 12 is joined to the structure of the one-shot cap 10 according to the invention by the circumferential attachment lip 17 when the cap 10 comes directly from the moulding process.

The one-shot cap 10 includes on its outer surface engagement accentuation means 18 which improve adhesion of the one-shot cap 10 to the skin.

The one-shot cap 10 according to the invention comprises fixture means 19 for the installation or removal of the cap 10 on or from the head 16 of the injector 11. In this example the fixture means 19 consist of an inner threaded portion 20 included on the inner surface of the cap 10 according to the invention; this inner threaded portion 20 cooperates with a coordinated outer threaded portion 21 included on the head 16 of the injector 11.

According to a variant the means 19 to fix the cap 10 to the head 16 of the injector 11 are embodied with a bayonet-type attachment or with a groove or another suitable means.

In this example the one-shot cap 10 according to the invention includes lengthwise engagement ribs 22 arranged on its outer surface.

In this case the one-shot cap 10 according to the invention comprises on its inner surface annular projections 23, which during the fitting of the cap 10 cooperate with the front end portion of the head 16 of the injector 11 and become deformed and improve the hydraulic seal engagement.

When the medicament has been charged into a chamber 27 of the injector 11 by retraction of a piston 28, the installation of the one-shot cap 10 thrusts backwards the striker 26 and thereby compresses a packing 29 slightly.

During charging of the chamber 27 the packing 29 has prevented the entry of air from outside into the chamber 27, so that the exact quantity of medicament is charged through a needle 30 from a phial 31 in a known manner.

When a trigger 24 is pressed, a spring 25 is released in a known manner and the piston 28 can slide axially in the chamber 27 and thrusts the medicament under pressure to the aperture 15 and therethrough to the hole 14 in the cap 10 in contact with the skin.

The medicament flows around the striker 26 owing to the play between the dimensions involved, overcomes by its pressure the resistance of the packing 29 and reaches the aperture 15.

The tapered conformation of the striker 26 in the zone of installment of the packing 29 assists the functioning.

The piston 28, when it reaches the end of its travel, beats against the striker 26 and thrusts it towards the removable stopper 12, possibly making use also of the field of elasticity of the packing 29.

By means of this movement the striker 26 thrusts the removable stopper 12 and breaks at least partly the attachment lip 17 which joins the stopper 12 to the one-shot cap 10, thus making the latter unusable.

According to the variant shown in FIG. 3 the striker 26 is annular and is positioned outside, around and on the same axis as the aperture 15 for the outflow of the medicament. In this case the striker 26 is not affected by the movement of the medicament.

The piston 28 is equipped with a ring 32 which is so positioned that it abuts against one or more small lateral pistons 33 when the piston 28 reaches substantially the end of its travel.

The small lateral pistons 33 in turn abut against a terminal protrusion 34 of the striker 26, thus causing the striker 26 to advance and, as a result, to break the attachment lip 17 of the removable stopper 12.

This embodiment includes valve means 35 in a central axial position between the aperture 15 and the medicament containing chamber 27. These valve means 35 prevent the entry of air from outside into the containing chamber 27 during charging of the medicament from a phial 31 (not shown in FIG. 3).

The piston 28, being actuated by spring means 25 (not shown in FIG. 3), thrusts the medicament under pressure and causes the opening of the valve means 35.

According to a further variant, resilient means 36 to cause retraction are included and bring the striker 26 to the injection position when the thrust action of the small lateral pistons 33 has ended. These resilient means 36 causing retraction possess a very slight strength which cannot offer great resistance to the thrust exerted by the small lateral pistons 33 against the striker 26.

The embodiment shown in FIG. 3 ensures a better hydraulic seal engagement within the chamber 27 and prevents any residues of medicament staying in any small spaces between the striker 26 and the head 16 of the injector 11.

According to a variant the end of the striker 26 causing breakage can be cut at a slant so as to assist breakage of the cap 10.

The aperture 15 according to the invention has a diameter such as to make impossible a transcutaneous injection without the presence of the one-shot cap 10.

It should be borne in mind that the diameter of the removable stopper 12 should be equal to or greater than the diameter of the front end of the striker 26.

I claim:

1. An injector for administering subcutaneous injections without a needle, comprising:
   an injection head having an aperture passing therethrough;
   a chamber operably connected to said aperture, said chamber having a piston axially movable therein, said piston having a retracted position enabling charging of medicament into said chamber and an expulsion position whereby said medicament is expelled from said chamber through said aperture when said piston is thrusted axially from said retracted position to said expulsion position;
   means for charging medicament into said chamber;
   means for thrusting said piston from said retracted position to said expulsion position;
   a replaceable, one-shot cap removably installed on said injection head, said cap having a removable stopper capable of being at least partly broken away from said cap and a hole through said removable stopper and cooperating with said aperture through which said medicament can pass; and
   an axially movable striker positioned within said injection head and cooperating with said piston and having a retracted position between said piston and said removable stopper and a breakage position projecting from said injection head for at least partly breaking said removable stopper away from said cap when said piston is in said expulsion position.

2. Injector as in claim 1 wherein said cap comprises engagement accentuation means on its front outer surface.

3. Injector as in claim 1, wherein said cap comprises annular projections on its inner surface to improve hydraulic seal engagement with said injection head.

4. Injector as in claim 1, wherein said removable stopper is connected to said cap by a peripheral attachment lip of reduced thickness which can be broken in a pre-set manner.

5. Injector as in claim 1, wherein said removable stopper has a diameter equal to or greater than that of a front end of said striker.

6. Injector as in claim 1, wherein said striker cooperates with a packing for preventing air from entering said chamber during charging of said medicament, the zone of such cooperation having a tapered conformation to enable medicament to flow from said chamber, around said packing and to said aperture.

7. Injector as in claim 1, wherein said striker is within and substantially axial to and able to move in relation to said injection head.

8. Injector as in claim 1, wherein said striker is located coaxial with, and surrounds, said aperture and cooperates with at least one small lateral piston and with ring means associated with said piston.

9. Injector as in claim 1, wherein said striker is positioned between said removable stopper and said piston in a substantially axial position.

10. Injector as in claim 1, wherein said aperture has a diameter substantially greater than that of said hole in said cap.

* * * * *